(12) United States Patent
Barbut

(10) Patent No.: US 6,896,663 B2
(45) Date of Patent: May 24, 2005

(54) RETROGRADE VENOUS PERFUSION WITH ISOLATION OF CEREBRAL CIRCULATION

(75) Inventor: Denise R. Barbut, New York, NY (US)

(73) Assignee: CoAxia, Inc., Maple Grove, MN (US)

( * ) Notice: Subject to any disclaimer, the term of this patent is extended or adjusted under 35 U.S.C. 154(b) by 257 days.

(21) Appl. No.: 10/143,334

(22) Filed: May 7, 2002

(65) Prior Publication Data

US 2002/0128586 A1 Sep. 12, 2002

Related U.S. Application Data

(63) Continuation of application No. 09/285,939, filed on Apr. 2, 1999, now Pat. No. 6,383,172.

(51) Int. Cl.[7] .............................................. A61M 37/00
(52) U.S. Cl. ..................................................... 604/6.14
(58) Field of Search ....................... 604/4.01, 8, 26–28, 604/43, 6.11, 6.13–6.14, 6.16, 500, 505, 507–509, 93.01, 95.03, 96.01, 94.01, 98.01, 101.04, 101.03, 102.01–102.03, 113, 264, 523–533, 538–39, 912, 915; 606/20–22, 191–194; 600/301, 363, 433–35, 481, 483, 485–86, 488; 422/44; 128/898, 905, DIG. 3–13

(56) References Cited

U.S. PATENT DOCUMENTS

| | | | |
|---|---|---|---|
| 5,011,468 A | * | 4/1991 | Lundquist et al. ............ 600/18 |
| 5,186,713 A | | 2/1993 | Rabile |
| 5,794,629 A | | 8/1998 | Frazee |
| 5,807,318 A | | 9/1998 | St. Goar et al. |
| 5,865,789 A | | 2/1999 | Hattler |
| 5,908,407 A | | 6/1999 | Frazee et al. |
| 6,110,139 A | * | 8/2000 | Loubser ....................... 604/30 |
| 6,482,171 B1 | * | 11/2002 | Corvi et al. ............. 604/96.01 |
| 6,555,057 B1 | * | 4/2003 | Barbut et al. .................. 422/44 |

OTHER PUBLICATIONS

Juvonen et al., Cardiopulmonary Support and Physiology, "Can Retrograde Perfusion Mitigate Cerebral Injury After Particulate Embolization? A Study in a Chronic Porcine Model," J. Thorac. and Cardiovasc. Surg., 115(5):1142–1159 (1998).

* cited by examiner

Primary Examiner—Patricia Bianco
(74) Attorney, Agent, or Firm—O'Melveny & Myers LLP

(57) ABSTRACT

A medical device for providing retrograde venous perfusion to the cerebral vasculature for treatment of global or focal cerebral ischemia is disclosed. The device includes a catheter having an infusion port at its distal end, venous drainage port(s), and an expandable occluder disposed between the infusion port and drainage port(s). The catheter can be inserted into the superior vena cava or the internal jugular vein. The catheter is attached proximally to a pump and an oxygenator with or without a cooling system. Alternatively, the device includes two catheters, each having a lumen communicating with a distal infusion port and an occluder mounted proximal to the port. The catheters can be inserted into the internal jugular veins distal to jugular venous valves. Methods of using the devices to provide retrograde venous perfusion and isolated cerebral hypothermia are disclosed.

10 Claims, 7 Drawing Sheets

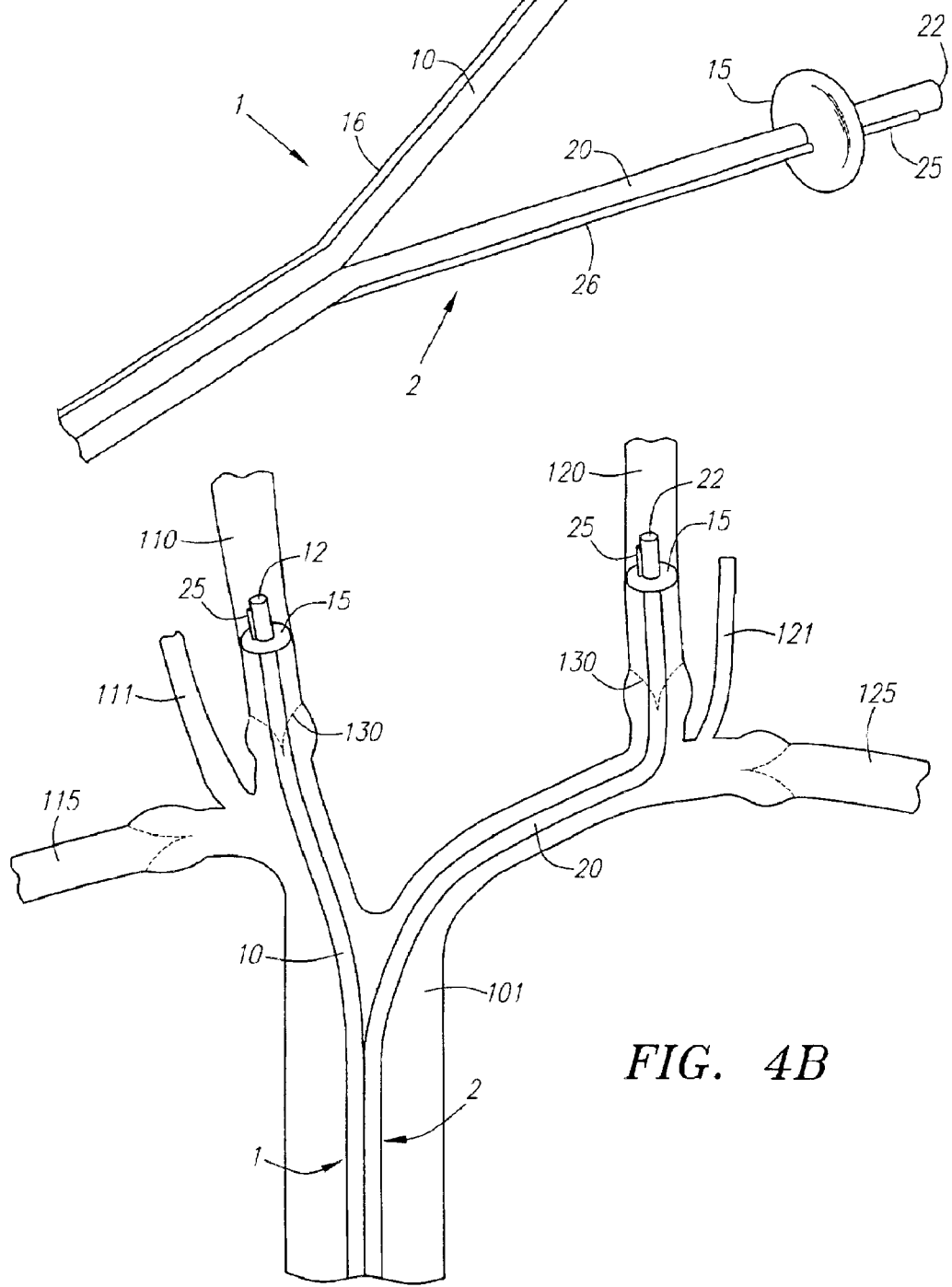

RETROGRADE VENOUS PERFUSION WITH ISOLATION OF CEREBRAL CIRCULATION

This is a continuation of U.S. application Ser. No. 09/285,939, filed Apr. 2, 1999, now issued as U.S. Pat. No. 6,383,172, the contents of which are expressly incorporated herein by reference.

FIELD OF THE INVENTION

The present invention generally relates to devices and methods useful in maintaining cerebral perfusion during global or focal cerebral ischemia. More specifically, the devices and methods provide effective retrograde perfusion to the cerebral circulation through the superior vena cava or the internal jugular veins. Retrograde venous perfusion may be used with hypothermia to provide isolated cerebral cooling. The devices and methods are also useful in improving perfusion to other peripheral organs besides the brain.

BACKGROUND OF THE INVENTION

Cerebral ischemia refers to cessation or reduction of blood flow to the cerebral tissues. Cerebral ischmia can be characterized as either global or hemispherical. Hemispherical or focal ischemia refers to cessation or reduction of blood flow within the cerebral vasculature resulting from a partial or complete occlusion in the intracranial or extracranial cerebral arteries. Global ischemia refers to cessation or reduction of blood flow within the cerebral vasculature resulting from systemic circulatory failure from various causes, including aortic surgery, cardiac arrest, shock, and trauma. Circulatory arrest is often required in performing surgeries on the aorta, e.g., aneurysm repair, aortic dissection, endarterectomy of aortic atheroma, and aortic stenting. Blood flow through the aorta is often interrupted due to opening of the aorta for these surgical procedures. Cessation of systemic circulation therefore places a patient at great risk, particularly in the cerebral vasculature where ischemia can rapidly lead to irreversible neurologic damage.

Various techniques have been proposed to improve cerebral perfusion in a patient suffering from either global or focal ischemia. For example, conventional cardiopulmonary bypass is used during cardiovascular surgeries to maintain perfusion to peripheral organs during cardiac arrest. However, cardiopulmonary bypass is generally not useful when the aorta fails to remain intact during aortic surgeries. Retrograde aortic perfusion (RAP) has been proposed to improve cerebral perfusion by clamping the ascending aorta and perfusing the aorta in a retrograde direction through a peripheral arterial access, typically the femoral artery. Disadvantages associated with retrograde aortic perfusion include significant cerebral embolization from dislodgment of atheromatous material in the descending aorta and the aortic arch. Moreover, RAP is not useful for aortic procedures distal or proximal to a limited surgical region of the aorta.

Another technique for protecting the brain during global or focal ischemia is provided by hypothermic circulatory arrest (HCA). HCA is achieved by inducing marked systemic hypothermia prior to cessation or reduction of systemic circulation. There are several disadvantages associated the HCA. For example, during cardiac arrest from cardiac arrhythmia or aortic surgeries, the systemic circulation remains stopped, thereby placing the patient at significant risk of ischemia despite utilizing hypothermia. Moreover, HCA has been associated with systemic coagulopathy, typically disseminated intravascular coagulopathy. Therefore, aortic surgery performed with HCA is associated with relatively high mortality (approximately 20 percent).

Another proposed technique for cerebral perfusion is referred to as selective antegrade cerebral perfusion (SCP). SCP is achieved by introducing a catheter through the aorta into a carotid artery to perfuse the cerebral vasculature. However, cerebral embolization can occur from introduction of the catheter which can dislodge atheromatous material, often present at the take-off from the aorta. Cerebral embolization can also occur from dislodgment of atheromatous material by clamping or snaring of the carotid artery. Air embolization can also occur from insertion of the catheter in the aorta or the carotid artery.

Another technique for improving cerebral perfusion is provided by retrograde cerebral venous perfusion (RCP), which is achieved by clamping the inferior vena cava and introducing oxygenated blood through a catheter inserted in the superior vena cava. Flow is established in a retrograde direction up the vena cava into the brachial and jugular veins. However, there are several disadvantages associated with using the RCP. For example, a majority (approximately 80%) of the oxygenated blood will run off into the arms and/or the heart and lungs, with as little as 20% of the blood entering the brain. Secondly, valves in the jugular veins may obstruct blood flow into the intracranial venous system. The blood can flow outwardly through the extensive collateral circulation without perfusing the brain. The amount of blood returned to the aorta from the carotid arteries represents no more than approximately 5% of the blood initially introduced to the superior vena cava. Thirdly, such retrograde perfusion often results in an increase in cerebral pressure which further inhibits blood inflow. Arterial efflux to the cerebral vasculature is found by the inventor to disappear after 20 minutes. Therefore, during RCP, the venous flow rates and pressures required to achieve and maintain significant arterial efflux are highly variable.

For these reasons, it would be desirable to provide improved devices and methods for protecting the brain and cerebral vasculature of patients suffering from global or focal ischemia, without the risk of cerebral embolization or systemic side effects.

SUMMARY OF THE INVENTION

The present invention provides devices and methods for improving cerebral perfusion in patients suffering from focal or global ischemia. More specifically, the devices and methods provide oxygenated blood flow to the brain using retrograde venous perfusion, which can be used in conjunction with hypothermia. In one embodiment, the medical device comprises a catheter which includes an elongate tubular member having a proximal end, a distal end, and first and second lumens. The first lumen communicates with the proximal end and an infusion port at the distal end of the catheter. The second lumen communicates with the proximal end of the catheter and a drainage port proximal to the infusion port. In certain embodiments, the second lumen communicates with a plurality of drainage ports. An expandable occluder, which may be an elastomeric balloon in certain embodiments, is mounted on a distal region of the catheter between the infusion port and the drainage port. A manometer is mounted on the catheter distal to the occluder for measuring blood pressure distal to the occluder. The proximal end of the catheter is adapted for attachment to an oxygenator machine and/or a pump.

In another embodiment, the device comprises first and second catheters. Each of the two catheters has a lumen communicating with a proximal end and an infusion port at a distal end. An expandable occluder is mounted on a distal region of each of the catheters proximal to the infusion port. A manometer is mounted distal to each occluder. The first catheter and the second catheter are joined for a substantial length and are separated at their distal ends. In certain embodiments, the catheters are separated at their proximal ends. The proximal ends of the catheters are adapted for attachment to an oxygenator machine and/or a pump.

In still another embodiment, the device having two catheters described above may include a third lumen communicating with the proximal end of the catheter and a drainage port at its distal end. The drainage port is located proximal to the occluders. In certain embodiments, the third lumen communicates with 2, 3, 4, 5, 6, 7, or any other number of drainage ports. The proximal end of the catheter is adapted for attachment to a pump and/or an oxygenator.

In a first method of using the devices, the distal end of the catheter is inserted through a peripheral vein, e.g., the femoral vein, into the vena cava. The distal region of the catheter and the occluder are positioned in the superior vena cava (SVC), and the occluder is expanded to isolate blood flow in the SVC. Deoxygenated blood is withdrawn from the drainage port(s) and passed through the second lumen and the proximal end of the catheter, which is connected to an oxygenator. The oxygenated blood or medium is then infused into the first lumen and through the infusion port of the catheter to perfuse the cerebral tissues through the SVC in a retrograde fashion, thereby obviating the need for IVC clamping and backflow of oxygenated blood into the right atrium and the lungs which occurs with existing methods for retrograde cerebral venous perfusion (RCP). Infusion of oxygenated blood may be facilitated by a pump connected to the oxygenator and the proximal end of the first lumen. The infusion rate of oxygenated blood can be varied according to the venous pressure recorded by the manometer, which is mounted distal to the occluder.

In still another embodiment, retrograde venous perfusion can be achieved by inserting the distal end of the catheter in the right or the left internal jugular vein. The occluder is expanded to occlude the internal jugular vein. Deoxygenated blood is withdrawn from the vena cava, oxygenated by an oxygenator, and returned to the internal jugular vein to perfuse the cerebral tissues in a retrograde direction through the lumen and infusion port of the catheter. By positioning the catheter in the internal jugular vein to minimize backflow of oxygenated blood to the arm instead of the SVC, and by positioning the occluder distal to the jugular venous valves to minimize obstruction of blood flow to the intracranial venous system, the infusion rate of oxygenated blood can be reduced. The jugular venous pressure (JVP) is often obtained indirectly by measurement of the pulmonary artery pressure from a Swan-Ganz catheter, which is commonly inserted in patients having aortic surgery or hemodynamic instability. The pulmonary artery pressure, however, often fails to reflect the JVP due to the presence of jugular vein valves. The manometer, which is mounted distal to the occluder in the internal jugular vein, will provide a more accurate measurement of the JVP.

In another method, deoxygenated blood withdrawn from the drainage port is passed through an oxygenator and a cooling system. The cooled oxygenated blood or medium is then infused through the first lumen and the distal port of the catheter to provide isolated hypothermic and retrograde venous perfusion to the brain. In this way, complication associated with systemic hypothermic perfusion, e.g., disseminated intravascular coagulopathy, is avoided.

In another method, after venous blood withdrawn from the SVC is passed through an oxygenator, the oxygenated blood is passed through a pump which connects with the proximal end of the first catheter and a proximal end of a second catheter. The second catheter has a lumen communicating with a distal end inserted through the femoral artery and positioned within the femoral artery, the iliac artery, or the descending aorta. In this way, oxygenated blood is delivered to the brain and the lower extremities and/or other vital organs, such as the kidneys. During aortic surgeries, the space available for instrumentation on the aorta, e.g., insertion of cannula for cardiopulmonary bypass, is often limited. The methods described above provide perfusion to the peripheral organs during cardiac arrest without the need for instrumentation on the aorta, and therefore provide a superior alternative to conventional cardiopulmonary bypass.

In still another embodiment, retrograde venous perfusion can be achieved by inserting the distal ends of the first and second catheters in the respective right and the left internal jugular veins. The occluders, which are mounted on the distal regions of the catheters and proximal to the infusion ports, are expanded to occlude the internal jugular veins. Deoxygenated blood can be withdrawn from the vena cava or a peripheral vein, e.g., the femoral vein or the subclavian vein, and oxygenated. Oxygenated blood is then delivered retrograde to the cerebral tissues through the infusion ports of the catheters positioned in the internal jugular veins. Optionally, the oxygenated blood can be cooled before infusing into the jugular veins to provide isolated hypothermic perfusion to the cerebral tissues.

It will be understood that there are several advantages in using the devices and methods disclosed herein for protecting the brain and cerebral vasculature of patients suffering from global or focal ischemia. For example, compared with known techniques for retrograde cerebral venous perfusion (RCP), the retrograde venous perfusion of the invention (1) minimizes backflow of blood to the heart and/or the arms, thereby allowing lower infusion rates to be used, (2) eliminates the need for IVC clamping, thereby minimizing damage to the IVC, (3) positions the catheters distal to the jugular venous valves, thereby minimizing obstruction of blood flow by the valves, (4) provides isolated cerebral hypothermic perfusion, (5) provides an accurate measurement of the jugular venous pressure, and (6) provides perfusion to the brain, the lower extremities, and other vital organs during cardiac arrest. In addition, significant cerebral embolization associated with retrograde aortic perfusion (RAP) and selective antegrade cerebral perfusion (SCP) is avoided using the venous retrograde perfusion disclosed herein.

BRIEF DESCRIPTION OF THE DRAWINGS

FIG. 4A depicts another embodiment of a device for providing retrograde venous perfusion.

FIG. 4B depicts the device of FIG. 4A inserted in the internal jugular veins.

DETAILED DESCRIPTION

Figure 1:
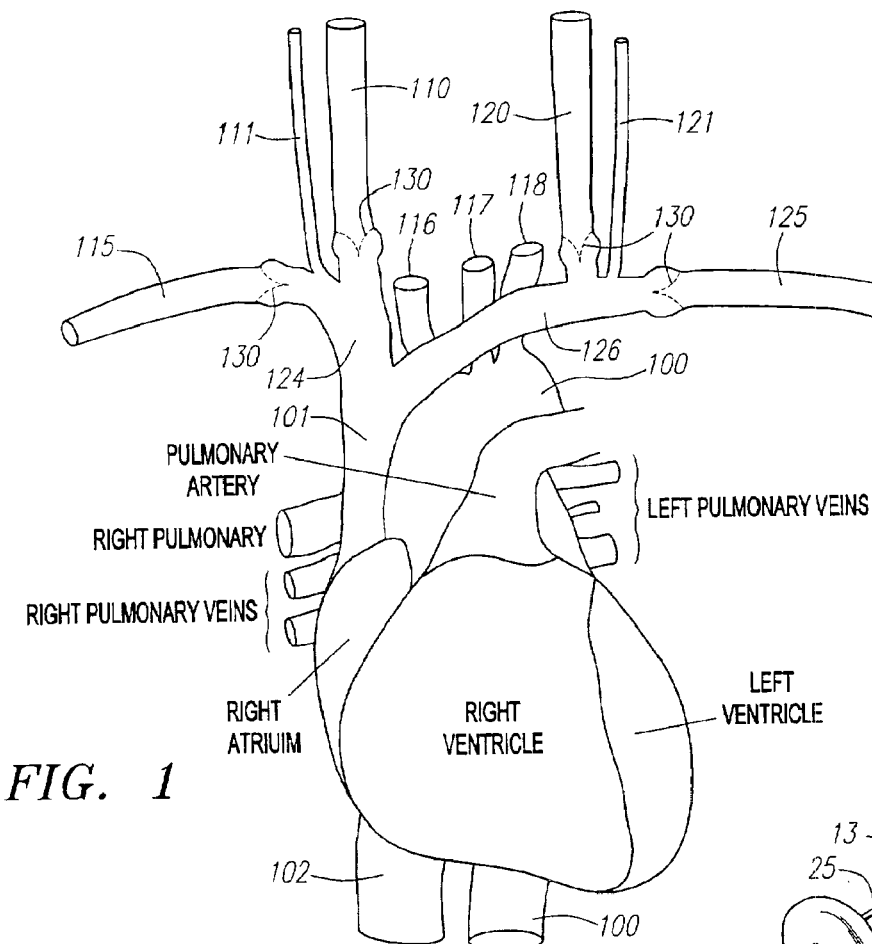
FIG. 1 depicts the cerebral venous system around the heart.

The cerebral venous system and the heart is depicted in FIG. 1. Arterial blood flow to the brain is normally supplied by aorta 100 which gives rise to right brachiocephalic trunk 116, left common carotid artery 117, and left subcalvian artery 118. Right internal jugular vein 110 and left internal jugular vein 120, usually the largest veins in the neck, drain blood from the brain and superficial parts of the face and neck. Right external jugular vein 111 and left external jugular vein 121 drain most of the scalp and face. Both the right external and internal jugular veins then drain into right brachiocephalic vein 124, and the left external and internal jugular veins drain into left brachiocephalic vein 126. The right brachiocephalic vein also receives drainage from right subclavian vein 115, and the left brachiocephalic vein receives drainage from left subclavian vein 125. The right and the left brachiocephalic veins drain into superior vena cava 101, which then empties into the right atrium. The right atrium also receives drainage from inferior vena cava 102. Venous valves 130 are included in the proximal segment of right subclavian vein 115, left subclavian vein 125, right internal jugular vein 110, and left internal jugular vein 121 to facilitate venous return to the heart.

Figure 2A:
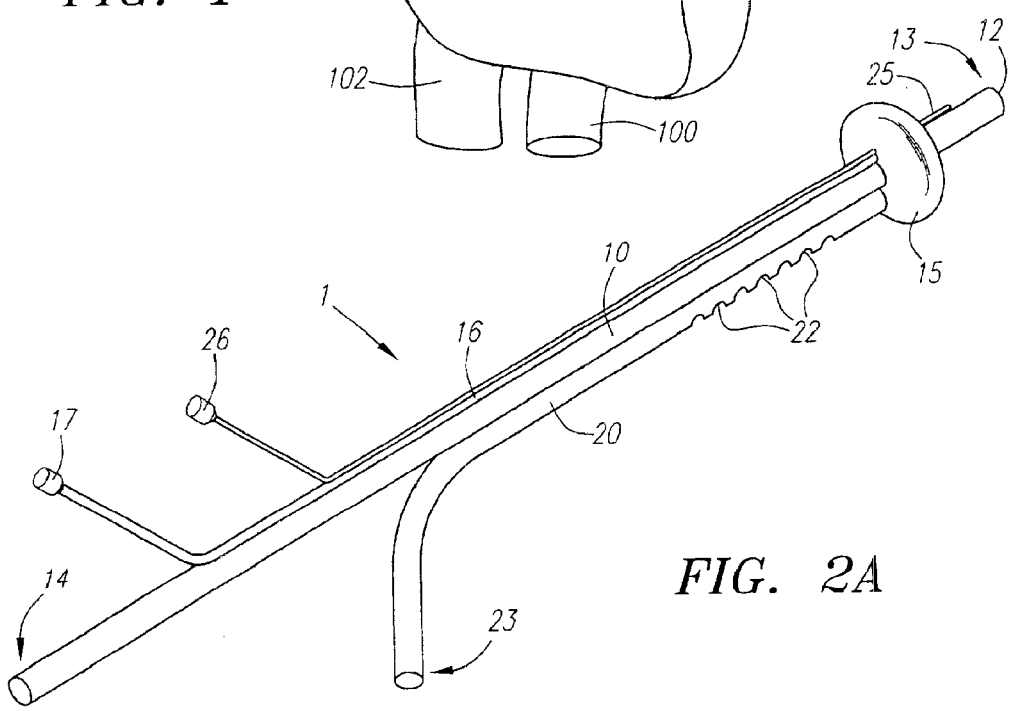
FIG. 2A depicts an embodiment of a catheter for retrograde venous perfusion according to the present invention.
Figure 2B:
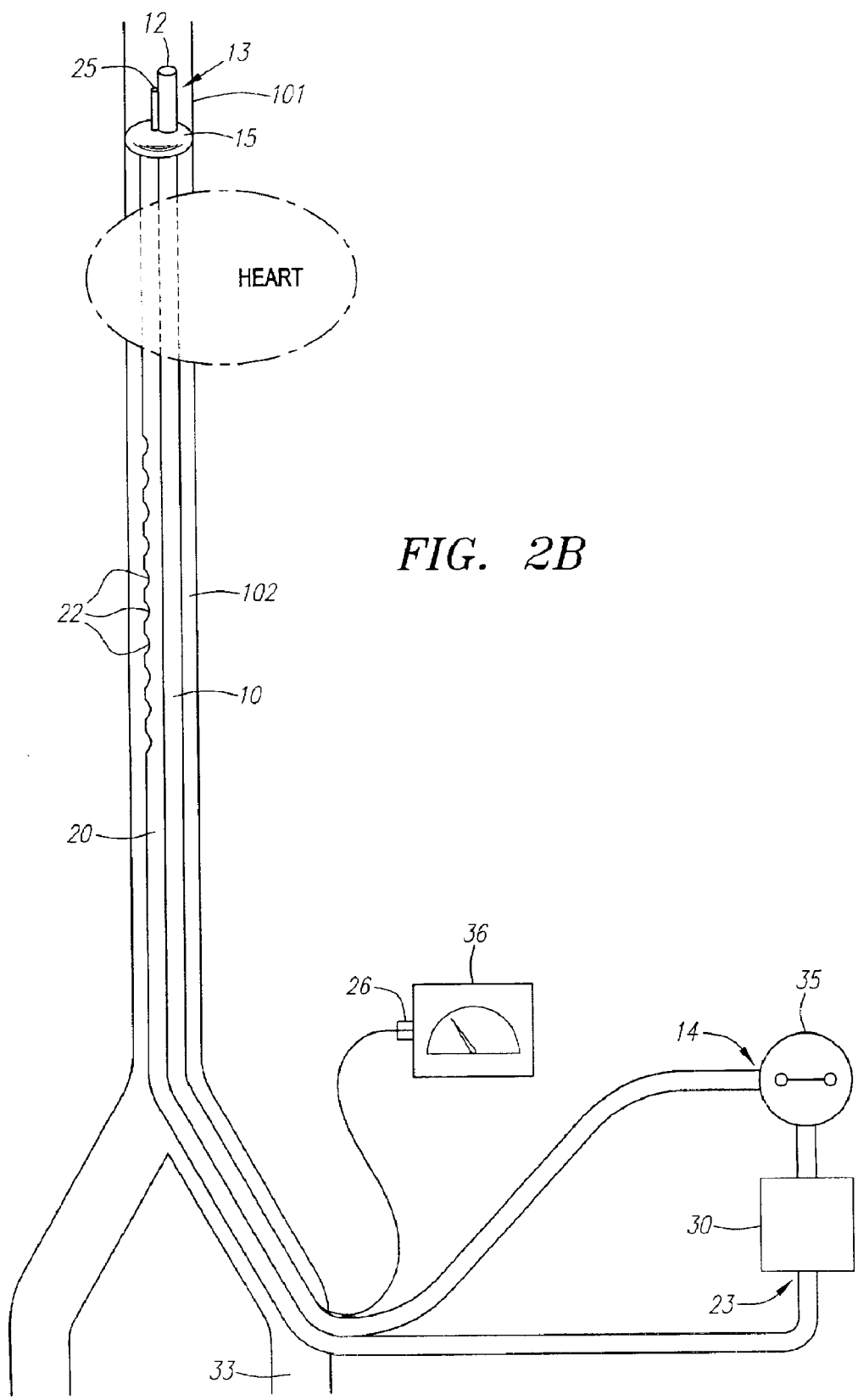
FIG. 2B depicts the catheter of FIG. 2A inserted in the superior vena cava.

An embodiment of the devices for the retrograde venous perfusion is depicted in FIGS. 2A and 2B. In FIG. 2A, catheter 1 has first lumen 10 and second lumen 20. The first lumen communicates with infusion port 12 at distal end 13, and with proximal end 14. The second lumen communicates with drainage ports 22 and proximal end 23. Expandable balloon occluder 15 is mounted on a distal region of the catheter proximal to infusion port 12 and communicates with inflation lumen 16 and inflation port 17. Either or both proximal end 14 and proximal end 23 of the respective first and second lumen is adapted for attachment to an oxygenator machine. Manometer 25 is mounted distal to occluder 15 and communicates with proximal end 26, which is adapted for attachment to a pressure monitor.

In use, as depicted in FIG. 2B, distal end 13 of the catheter is inserted through left femoral vein 33 into superior vena cava 101 via inferior vena cava 102 and the right atrium. Proximal end 23 of second lumen 20 is attached to bypass-oxygenator 30, and proximal end 14 of first lumen 10 is attached to pump 35. Pump 35 is connected to bypass-oxygenator 30. Occluder 15 is then expanded to occlude the SVC. Venous blood is withdrawn from drainage ports 22, passed through lumen 20, and oxygenated by bypass-oxygenator 30. The oxygenated blood is then passed through pump 35 which delivers the blood to first lumen 10 and infusion port 12 for providing retrograde venous perfusion to the cerebral vasculature from SVC 101. Manometer 25 measures the blood pressure distal to occluder 15 and connects by proximal end 26 to pressure monitor 36, which displays the pressure measurement. The infusion rate to the SVC is variably controlled by pump 35 according to the blood pressure measured in the SVC. In certain embodiments, oxygenator 30 includes a cooling system for delivering hypothermic oxygenated medium to the cerebral vasculature. When the distal end of the catheter is alternatively positioned in the internal jugular vein, the catheter provides isolated cooling of the cerebral tissues, thereby avoiding complications associated with hypothermic circulatory arrest (HCA).

Figure 3A:
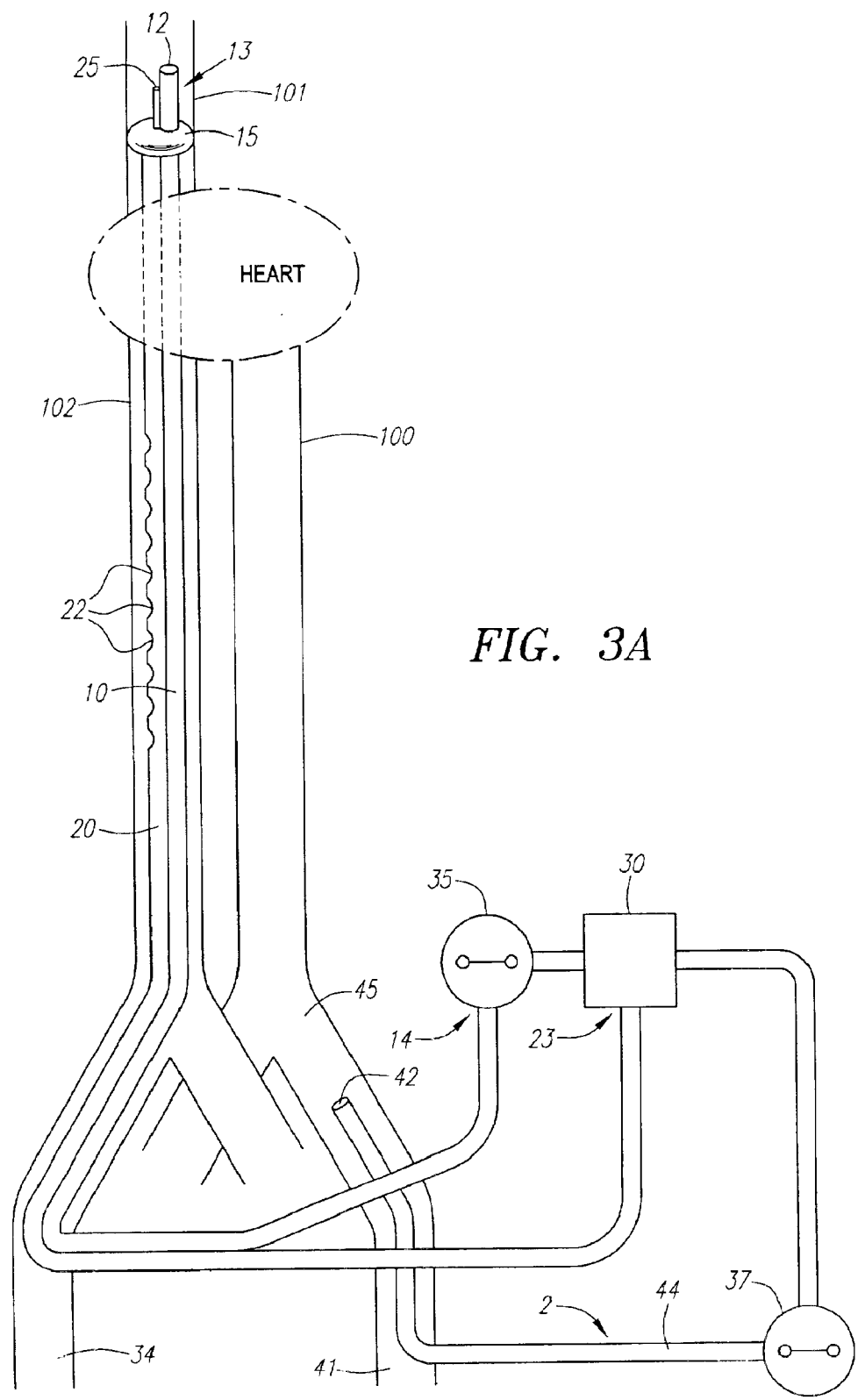
FIG. 3A depicts a second catheter inserted through the left femoral artery for providing perfusion to the peripheral organs.

In addition to maintaining cerebral perfusion during global or focal ischemia, the devices can be used to provide perfusion to the rest of the body organs, e.g., the lower extremities. In FIG. 3A, the catheter of FIG. 2A is inserted through right femoral vein 34 to an appropriate position in SVC 101 via inferior vena cava 102 and the right atrium. Proximal end 23 of second lumen 20 is attached to bypass-oxygenator 30. Oxygenator 30 is connected to first pump 35 and second pump 37, which is connected to catheter 2 inserted through left femoral artery 41. Catheter 2 has lumen 44 communicating with distal port 42, which is positioned in left iliac artery 45. In use, occluder 15 is expanded in SVC 101, and venous blood is withdrawn from drainage ports 22. Deoxygenated blood is passed through oxygenator 30 and delivered to pump 35 and pump 37. Pump 35 then delivers oxygenated blood to the SVC, whereas pump 37 delivers oxygenated blood to left iliac artery 45. In this way, retrograde perfusion of the cerebral tissues through the SVC and the lower extremities through the iliac artery can be variably and independently controlled, respectively, by pumps 35 and 37. The methods and devices described above are particularly useful in maintaining perfusion to peripheral organs during aortic surgeries with cardiac arrest, where the use of conventional cardiopulmonary bypass is limited by opening of the aorta.

Figure 3B:
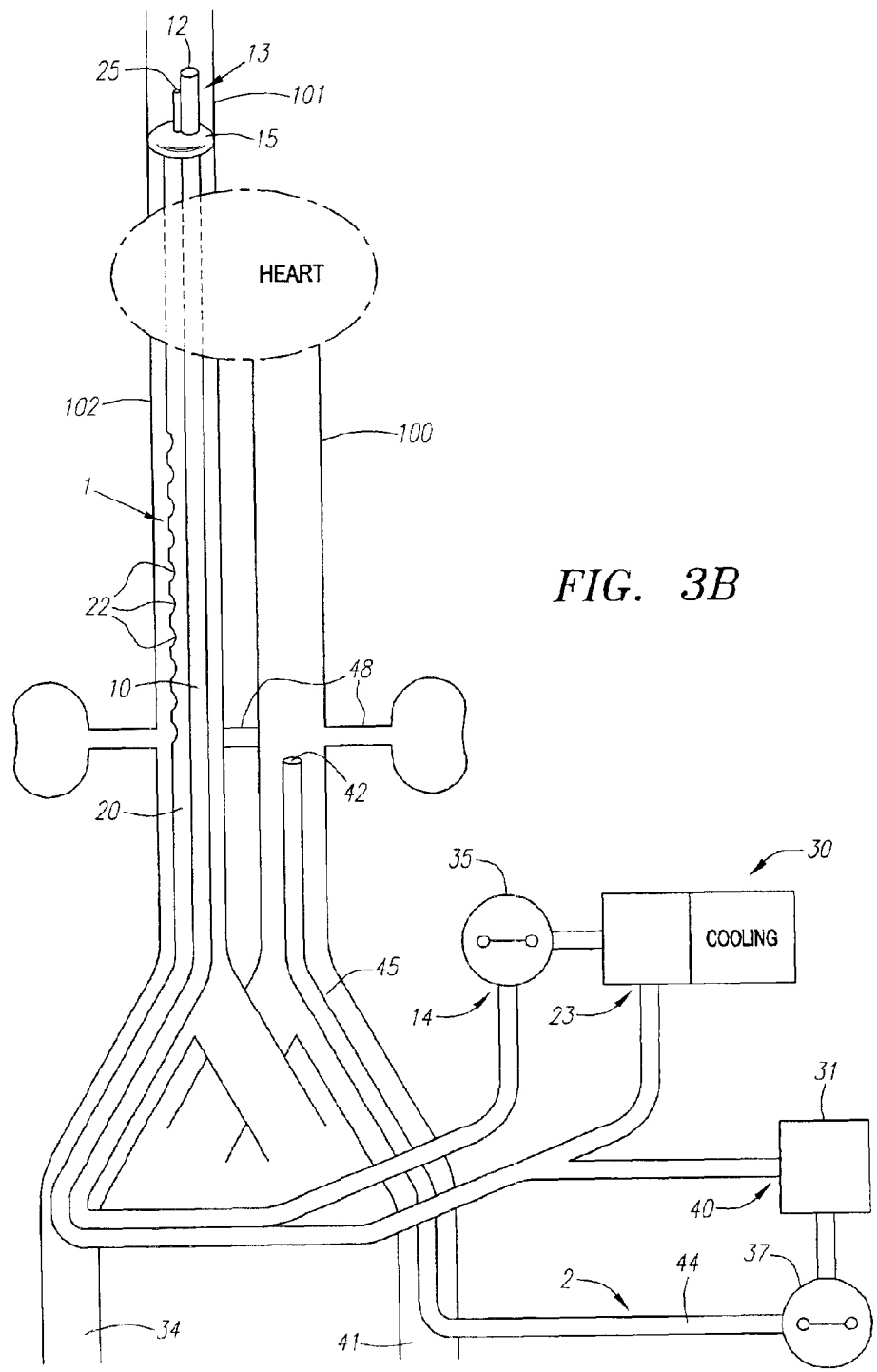
FIG. 3B depicts another embodiment of the catheter for providing perfusion to the brain and the peripheral organs.

In another embodiment of the catheter, lumen 20 communicates with proximal ends 23 and 40 as depicted in FIG. 3B. Proximal end 23 is attached to bypass-oxygenator 30 which includes a cooling system, whereas proximal end 40 is attached to bypass-oxygenator 31. Distal port 42 of second catheter 2 is inserted in descending aorta 100 in the proximity of renal arteries 48. In use, venous blood is withdrawn from IVC 102 through drainage ports 22 and delivered to oxygenator/cooler 30 and oxygenator 31. The cooled oxygenated blood (at between approximately 4° C. and 35° C., more preferably between 10° C. and 35° C., more preferably between 20° C. and 35° C.) is passed through pump 35 and delivered to SVC 101 through port 12, whereas oxygenated blood is passed through pump 37 and delivered to descending aorta 100 through port 42 of the second catheter. In this way, catheter 1 provides isolated cooling and retrograde perfusion to the cerebral tissues and the upper extremities, whereas catheter 2 provides retrograde perfusion at body temperature to the rest of the peripheral organs, including the kidneys.

The infusion rates of the two catheters can be independently controlled by pumps 35 and 37.

Another embodiment of the devices for providing retrograde venous perfusion is shown in FIG. 4A. Catheters 1 and 2 have, respectively, lumens 10 and 20 communicating with ports 12 and 22. Balloon occluders 15 are mounted on distal regions of catheters 1 and 2 proximal to the infusion ports. Manometers 25 are mounted distal to the occluders. Catheters 1 and 2 are joined for a substantial length at their mid regions and separated at the distal ends.

In use as shown in FIG. 4B, the distal ends of the catheters are inserted through a peripheral vein, e.g., the femoral vein, up through SVC 101 and positioned in the internal jugular veins. Port 12 of first catheter 1 is positioned in right internal jugular vein 110 distal to venous valves 130, whereas port 22 of second catheter 2 is positioned in left internal jugular vein 120 distal to venous valves 130. Balloon occluders 15 are inflated on the two catheters to occlude the jugular veins. Venous blood withdrawn from another peripheral vein, e.g., the femoral vein or the subclavian, is oxygenated and delivered to port 12 and 22 through respective lumens 10 and 20. Manometers 25 provide accurate measurements of jugular venous pressure (JVP) distal to the occluders. Flow rate of the oxygenated blood can be variably controlled according to the JVP. Since no backflow of blood occurs to the arms and the heart, and the infusion occurs past the jugular venous valves, much lower infusion rates are needed to provide retrograde venous perfusion to the cerebral tissues.

Figure 5:
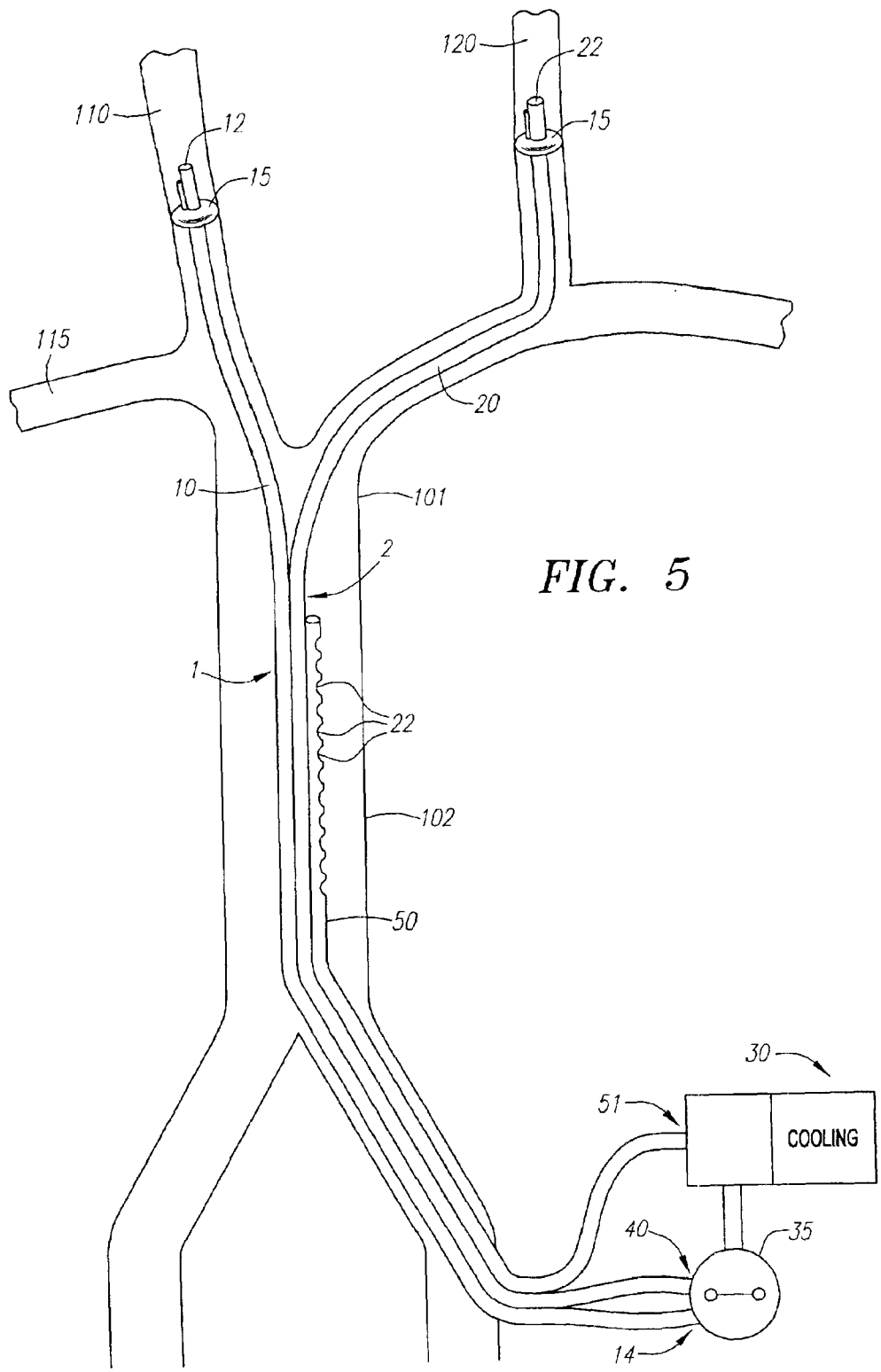
FIG. 5 depicts another embodiment of the device inserted in the internal jugular veins for providing retrograde venous perfusion.

FIG. 5 depicts another embodiment of the devices having third lumen 50 for providing retrograde venous perfusion to the internal jugular veins. Lumen 50 is joined to catheters 1 and 2 for a substantial length at a mid region and separated at its proximal end. Lumen 50 communicates with drainage ports 22 and proximal end 51 which is attached to oxygenator/cooler 30. In use, deoxygenated blood from inferior vena cava 102 is withdrawn and passed through oxygenator/cooler 30. Hypothermic oxygenated blood is then passed through pump 35, which is connected to proximal end 14 of lumen 10 and proximal end 40 of lumen 20, and delivered to right internal jugular vein 110 through port 12 and left internal jugular vein 120 through port 22. In this way, isolated cerebral hypothermia and retrograde venous perfusion is achieved without the complications of cerebral embolization associated with retrograde cerebral perfusion and coagulopathy associated with systemic cooling. By having third lumen 50 for venous drainage, only one entry site is needed for operation of the device.

Figure 6:
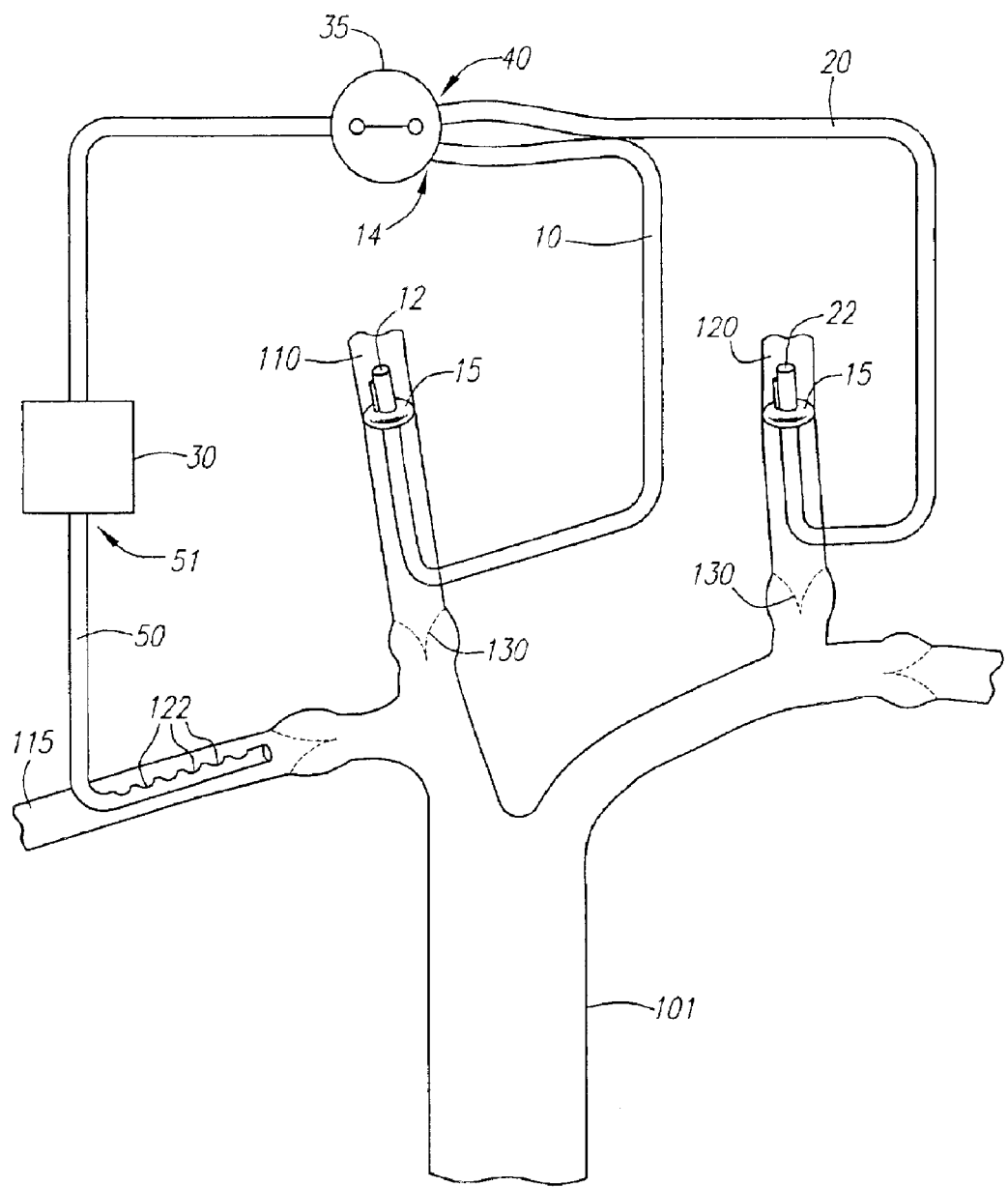
FIG. 6 depicts the device of FIG. 4A inserted in the internal jugular veins by direct stick.

In emergency situations, distal ends of catheters 1 and 2 can be inserted as a direct stick into the internal jugular veins distal to venous valves 130 as depicted in FIG. 6. A third catheter having lumen 50 communicating with drainage ports 122 can be inserted in a peripheral vein, e.g., right subclavian vein 115, to withdraw venous blood. Deoxygenated blood from right subclavian vein 115 is passed to oxygenator 30 through proximal end 51. Oxygenated blood is then delivered to port 12 in right internal jugular vein 110 and port 22 in left internal jugular vein 120 through lumens 10 and 20, respectively, to provide retrograde venous perfusion to the cerebral vasculature in patients with global or focal ischemia.

The length of the catheter will generally be between 30 and 200 centimeters, preferably approximately between 50 and 150 centimeters. The inner diameter of the catheter lumen will generally be between 0.2 and 0.8 centimeters, preferably approximately between 0.3 and 0.5 centimeters. The diameter of an expanded occluder will generally be between 0.3 to 2.0 centimeters, preferably approximately between 0.5 and 1.2 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. It must be further understood that cooling is an optional feature for each and every embodiment, and therefore must not be regarded as a required feature. The same is true for balloon occlusion as there are other known types of occlusion members.

What is claimed is:

1. A method for retrograde venous perfusion, comprising the steps of:

providing a catheter having a proximal end and a distal end that branches into first and second distal segments, each distal segment having a lumen and a distal region having an expandable occluder and an infusion port located distal the occluder, the catheter further comprising a lumen extending from the proximal end and communicating with the lumen and infusion port of the first distal segment and the lumen and infusion port of the second distal segment;

inserting the first distal segment into a first internal jugular vein;

expanding the occluder on the first distal segment within the first internal jugular vein;

inserting the second distal segment into a second internal jugular vein;

expanding the occluder on the second distal segment within the second internal jugular vein;

inserting the proximal end of the catheter into the right subclavian vein;

withdrawing blood from the right subclavian vein;

oxygenating the withdrawn blood; and infusing oxygenated medium into the first and second internal jugular veins through the lumens and infusion ports of the first and second distal segments, wherein oxygenated medium is returned to the cerebral tissues by retrograde venous perfusion.

2. The method of claim 1, wherein the first and second distal segments are inserted at a location upstream one or more valves within the jugular veins before the occluders are expanded.

3. The method of claim 1, wherein the first and second distal segments are advanced to a position upstream one or more valves within the jugular veins before the occluders are expanded.

4. The method of claim 1, wherein the expandable occluders of the first and second distal segments are balloon occluders.

5. The method of claim 1, wherein the first and second distal segments further comprise manometers located distal the occluders for measuring jugular venous pressure.

6. The method of claim 1, wherein the first distal segment is inserted into the first internal jugular vein through the vena cava and the femoral vein.

7. The method of claim 1, wherein the second distal segment is inserted into the second internal jugular vein through the vena cava and the femoral vein.

8. The method of claim 1, wherein the oxygenated medium is blood.

9. The method of claim 1, wherein the oxygenated medium is hypothermic.

10. The method of claim 1, wherein oxygenated medium from an oxygenator machine is returned to the lumens of the first and second distal segments.

* * * * *